United States Patent [19]

Greenwood et al.

[11] Patent Number: 4,923,443
[45] Date of Patent: May 8, 1990

[54] SINGLE USE SYRINGE

[76] Inventors: Eugene C. Greenwood, 2956-B Pepper Tree La., Costa Mesa, Calif. 92626; John A. Holland, 1836 Port Abbey Pl., Newport Beach, Calif. 92660

[21] Appl. No.: 253,137
[22] Filed: Oct. 4, 1988
[51] Int. Cl.⁵ .............................................. A61M 5/00
[52] U.S. Cl. .................................... 604/110; 604/228
[58] Field of Search ................ 604/110, 218, 228, 187

[56] References Cited

U.S. PATENT DOCUMENTS 4,775,363 10/1988 Sandsdalen ......................... 604/110
4,775,364 10/1988 Alles ................................... 604/110

Primary Examiner—John D. Yasko
Attorney, Agent, or Firm—Roy A. Ekstrand

[57] ABSTRACT

A single use hypodermic syringe uses a generally cylindrical elongated syringe body defining a center bore and supporting a hollow needle in communication with the center bore. A movable piston preferably formed of rubber or resilient plastic material is sealingly supported within the syringe bore. A driver member extends into the syringe bore and is coupled to the piston by a single use coupling. Several embodiments of the single use coupling are shown which function to preclude any further use of the syringe once the fluid injection operation has been implemented by the syringe.

10 Claims, 2 Drawing Sheets

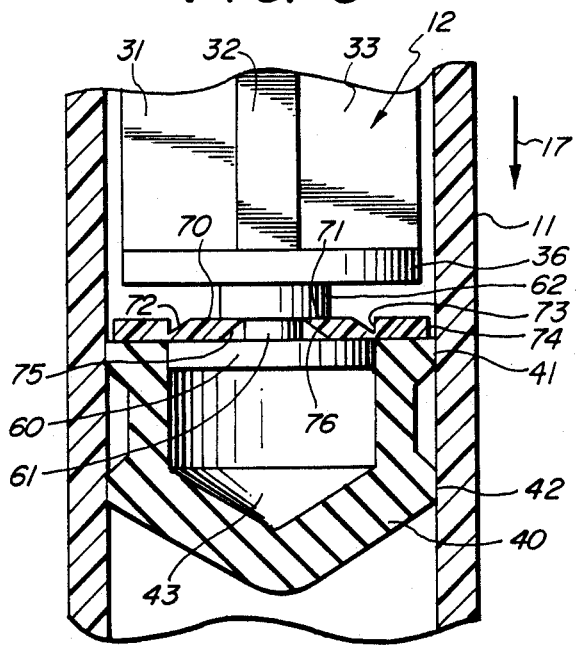
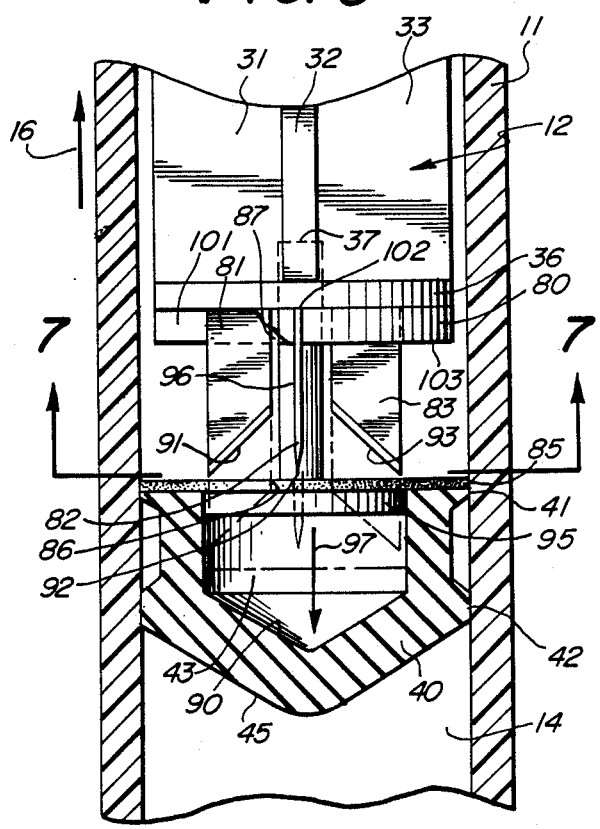
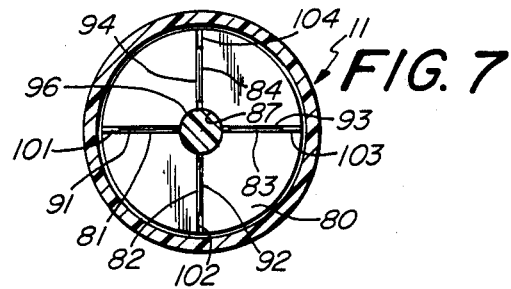
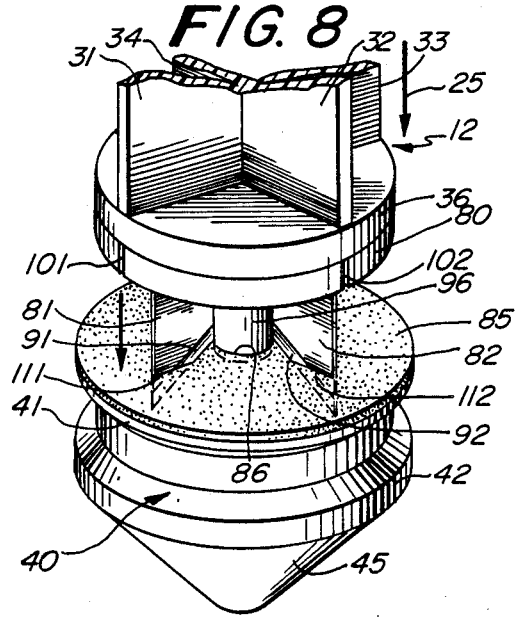
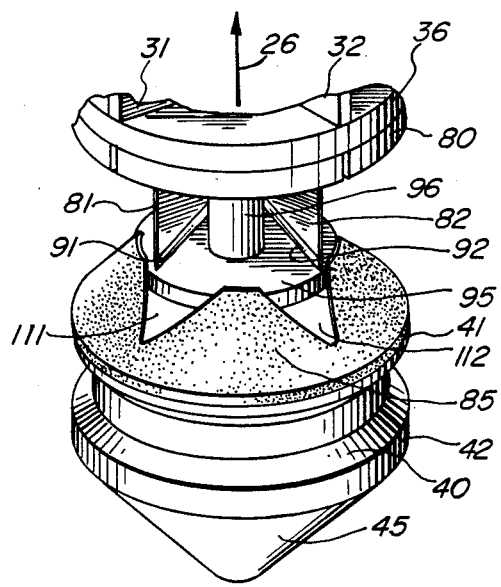

SINGLE USE SYRINGE

FIELD OF THE INVENTION

This invention relates generally to hypodermic syringes and particularly to a mechanism by which such hypodermic syringes are incapable of multiple use.

BACKGROUND OF THE INVENTION

In the medical arts, one of the more commonplace devices is the hypodermic syringe which is used to inject a quantity of fluid beneath the skin of a patient. While the structures of such hypodermic syringes vary with design choice, all generally include a cylindrical barrel defining a central cylindrical bore which terminates at one end in a restricted passage in communication with an outwardly extending hollow pointed needle. The remaining end is generally open and receives a piston assembly which includes an elongated driver supporting a piston. The piston is sized to sealingly slide within the bore of the syringe barrel and thereby control the volume confined within the interior of the syringe bore between the end needle passage and the piston.

In typical use, the needle is inserted into a small container after which the piston driver is drawn outwardly from the syringe barrel moving the piston away from the needle passage and drawing a quantity of the to-be-injected fluid into the syringe bore. Thereafter, the needle is withdrawn from the container and the syringe is pointed upwardly. The piston driver is then moved into the syringe bore a short distance to expel any trapped air from the syringe interior making the syringe ready for use. As a final step, the needle is inserted into or beneath the skin of the patient and the driver is moved inwardly within the syringe bore to expel the desired quantity of fluid into the patient's system. Finally, the needle is withdrawn from the patient's skin and discarded.

While syringes manufactured and used by the medical profession today are generally intended for a single use, in fact their structures are often sufficiently sturdy to facilitate multiple-use by persons obtaining them through various unauthorized means. Most prevalent among such unauthorized users of hypodermic syringes are intravenous drug users who often use such syringes repeatedly and in many cases exchange syringes with fellow intravenous drug users.

While a problem of infection and disease proliferation has usually accompanied such unauthorized use of syringes by intravenous drug users, the recent increase in the disease known as Acquired Immune Deficiency Syndrome (AIDS) has greatly increased the alarm of the medical profession at such unauthorized use of discarded syringes.

Through the years, a number of hypodermic syringes have been developed which are directed to increasing the safety of use of hypodermic syringes. One such device is set forth in U.S. Pat. No. 3,306,290 issued to Weltman which sets forth an AUTOMATICALLY RETRACTABLE NEEDLE SYRINGE having an elongated tubular body defining a central bore and a slidable piston assembly therein. A hub mounted on the body portion defines an axial bore, receives the needle portion of the syringe and provides a safety member therefor.

U.S. Pat. No. 4,258,713 issued to Wardlaw sets forth an AUTOMATIC DISPOSABLE HYPODERMIC SYRINGE in which a disposable syringe includes a retracted needle which is driven by a spring to administer an injection. The needle is contained within a housing and is driven from the housing to administer the injection. A release mechanism is provided to operate the syringe.

U.S. Pat. No. 4,188,950 issued to Wardlaw sets forth a DISPOSABLE SYRINGE in which provisions are made for rendering the needle incapable of harming anyone once the unit is discarded. The syringe operates with a retracted needle which is driven to a protruding position when the device is used. After use the needle is retracted from the protruding position and is bent to prevent the needle from harming anyone and to prevent reuse of the needle.

U.S. Pat. No. 4,139,009 issued to Alvarez sets forth a HYPODERMIC NEEDLE ASSEMBLY WITH RETRACTABLE NEEDLE COVER in which a disposable hypodermic needle assembly includes a permanently attached but retractable covering means for the forward portions of the needle. The covering means include an annular slide member slidable with respect to the needle and normally positioned to cover the forward or pointed portion of the needle. A plurality of elastically resilient arms support the slide member in the covering position but may be withdrawn therefrom by sliding the slide member down the needle shaft and overcoming the elasticity of the resilient arms. Once the needle is used, the resilient arms return the slide member to the covering position and means are provided for locking the slide member in the covering position.

U.S. Pat. No. 4,507,117 issued to Ryan, et al. sets forth a SYRINGE APPARATUS WITH RETRACTABLE NEEDLE in which a syringe apparatus includes a syringe barrel and internal movable piston as well as an extending needle portion in communication therewith. A first locking member locks the needle in the extended position while a second locking member locks the needle to the slidable piston within the syringe barrel. In use, the needle is initially locked in the extending position and injection is administered. Thereafter, the needle may be unlocked from the extended position and retracted into the barrel by locking the needle to the piston and drawing the piston inwardly pulling the needle into the barrel interior.

U.S. Pat. No. 4,378,015 issued to Wardlaw sets forth an AUTOMATIC INJECTING SYRINGE in which a hypodermic needle employs a retracted needle contained within the syringe housing. The syringe is fabricated from a minimum number of parts and is intended to be inexpensively and easily assembled. A safety feature is included which prevents accidental operation of the syringe.

While the foregoing described prior art devices provide some protection and increased safety of the use of hypodermic syringes and some prevention of the reuse thereof, they often render the hypodermic syringe more costly to manufacture and more cumbersome to use. In addition, several of the prior art structures, such as those described above intended to render the hypodermic syringe limited to a single use, require a special action on the part of the medical professional to assure the non-reuse of the hypodermic syringe. The need for additional manipulation of the syringe to render it incapable of further use imposes an undesirable burden on the medical professional and raises the possibility of reusable syringes being available.

There remains, therefore, a need in the art for a convenient to use, inexpensive to manufacture hypodermic syringe which is limited to a single use. There remains a further need for such a single use syringe which is automatically rendered inoperative following its normal use by the medical professional.

SUMMARY OF THE INVENTION

Accordingly, it is a general object of the present invention to provide an improved hypodermic syringe. It is a more particular object of the present invention to provide an improved hypodermic syringe designed for a single use. It is a still more particular object of the present invention to provide an improved hypodermic syringe for single use which is automatically rendered inoperable following its first use.

In accordance with the invention, there is provided a single use syringe having an elongated syringe body supporting a movable piston therein and coupled to a hypodermic needle. A driver extends into the interior of the syringe body and is coupled to the piston by coupling means which render the syringe inoperable once the piston has been driven forward within the syringe body.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 5 sets forth a partial section view of the present invention single use hypodermic syringe during the forward stroke of the piston;

FIG. 6 sets forth a partial section view of an alternate embodiment of the present invention single use hypodermic syringe;

FIG. 7 sets forth a cross section view of the present invention single use hypodermic syringe taken along section lines 7—7 in FIG. 6.

FIG. 8 sets forth a partial perspective view of the alternate embodiment of the present invention single use syringe set forth in FIG. 6 at the beginning of a forward piston motion; and FIG. 9 sets forth a partial perspective view of the embodiment of FIG. 8 during an attempted withdrawal of the piston following the first use of the present invention single use syringe.

DESCRIPTION OF THE PREFERRED EMBODIMENTS

Figure 1:
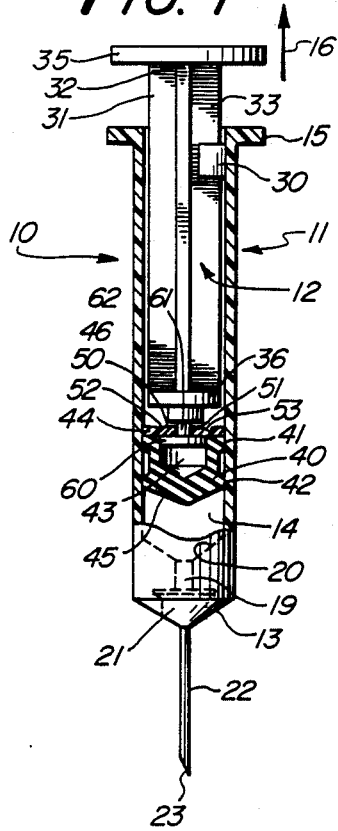
FIG. 1 sets forth a partially sectioned side view of a single use hypodermic syringe constructed in accordance with the present invention.

FIG. 1 sets forth a partial section view of a hypodermic syringe 10 constructed in accordance with the present invention. Syringe 10 includes an elongated generally cylindrical syringe body 11 defining a flange 15 at one end and a taper 13 at the other end. Syringe body 11 further defines an interior generally cylindrical syringe bore 14 extending from flange 15 to a funnel end 20 proximate taper 13. A needle retainer 21 is supported within syringe body 11 proximate taper 13 and in turn supports an elongated hollow needle 22 defining a point 23. A passage 21 defined within syringe body 11 extends from funnel end 20 to needle retainer 21 and provides communication between needle 22 and bore 14. A piston 40, preferably formed of a resilient rubber material or the like, defines a pair of outwardly extending rib seals 41 and 42 which form sealing contact with the interior of bore 14. Piston 40 further defines an interior cavity 43. A beam plate 44 having a generally planar annular structure is fitted within bore 14 and is attached to piston 40. Beam plate 44 further defines a center aperture 46 and a pair of inwardly extending beam members 50 and 51. A pair of fulcrums 52 and 53 join beam members 50 and 51 respectively to beam plate 44.

A driver 12 is formed of a quartet of outwardly extending rib members 31, 32, 33 and 34 (the latter not shown). Ribs 31 through 34 are commonly joined and generally perpendicularly arranged to provide an elongated rigid driver capable of supporting substantial compressive forces. Driver 12 further defines a knob 35 and an end flange 36 at opposite ends of ribs 31 through 34. A breaker ring 62 extends downwardly from end flange 36 and forms a generally cylindrical extension thereof. A retractor shaft 61 having a diameter smaller than aperture 46 of beam plate 44 extends from breaker ring 62 through aperture 46 to the interior of cavity 43 of piston 40. A generally planar cylindrical retractor head 60 is joined to retractor shaft 61 within cavity 43. Thus, retractor head 60 is captivated within cavity 43 by beam plate 44 and beams 50 and 51 and is joined to breaker ring 62 by retractor shaft 61.

An inwardly extending lock member 30 is joined to the interior of bore 14 of syringe body 11 and positioned between ribs 32 and 33. The function of lock member 30 is to captivate driver 12 within syringe bore 14 of syringe body 11 while still permitting the axial movement of driver 12 within bore 14. This precludes tampering with the syringe and inactivating its self-destruct mechanism prior to using it. Accordingly, lock 30 is positioned between ribs 32 and 33 in a noninterfering alignment which permits driver 12 to be drawn outwardly from syringe body 11 until end flange 36 contacts lock member 30. Thereafter, further outward movement of driver 12 is precluded by the interference of end flange 36 and lock member 30.

In operation, hypodermic syringe 10 is initially assembled with piston 40 positioned at the bottom of bore 14 such that cone surface 45 is in contact with funnel end 20. In the assembled position, driver 12 is coupled to piston 40 by the captivation of retractor head 60 within cavity 43 by beam plate 44. In accordance with conventional operation of hypodermic syringes, point 23 of needle 22 is inserted into a container having the to-be-injected fluid therein. Once point 23 of needle 22 is beneath the surface of the to-be-injected fluid, knob 35 of driver 12 is drawn outwardly in the direction indicated by arrow 16 which in turn brings retractor head 60 into contact with the undersides of beam 50 and 51. In accordance with an important aspect of the present invention, the planar configuration of retractor head 60 and the extended diameter of retractor head 60 cooperate to apply the force applied to beam members 50 and 51 close to fulcrums 52 and 53 respectively. As is described below in greater detail, the application of force by retractor head 60 to beams 50 and 51 close to fulcrums 52 and 53 respectively couples the force through very short lever arms for the force. This permits piston 40 to be drawn upwardly within bore 14 without breaking beams 50 or 51. In accordance with the preferred fabrication of the embodiment of the present invention shown in FIG. 1, beam plate 44 is constructed of a brittle material such as acrylic. Once piston 40 has been drawn upwardly within bore 14 of syringe body 11, the to-be-injected fluid is drawn into the interior of bore 14.

Thereafter, with the desired volume of to-be-injected fluid supported within bore 14 and captivated by piston 40, syringe 10 is reoriented such that needle 22 points upwardly and driver 12 is moved into syringe body 11 a short distance to expel any trapped air within bore 14 and the interior of hollow needle 22. Once the trapped air has been expelled, point 23 of needle 22 is forced through the patient's skin to the desired interior portion of the patient's anatomy and driver 12 is forced inwardly with respect to syringe body 11 which in turn drives piston 40 downwardly within bore 14 and forces the captivated fluid outwardly from bore 14 through needle 22 to accomplish the desired injection.

By means set forth below in greater detail, the forward stroke of driver 12 which moves piston 40 downwardly causes breaker ring 62 to break beam 50 and 51. With beams 50 and 51 broken, retractor head 60 is moved downwardly within cavity 43 of piston 40 and end flange 36 contacts beam plate 44 and thereafter couples the downward force of driver 12 to piston 40.

In accordance with an important aspect of the present invention, however, once the foregoing sequence of operations has occurred resulting in the severing or breaking of beam members 50 and 51, any attempt to draw piston 40 outwardly within bore 14 results in simply pulling retractor head 60 through beam plate 44 which because of the previous severing of beams 50 and 51 offers no resistance to retractor head 60 permitting it to simply be withdrawn from piston 40. Thus, by the foregoing operation, driver 12 is no longer operatively coupled to piston 40 and syringe 10 is rendered inoperative.

Figure 2:
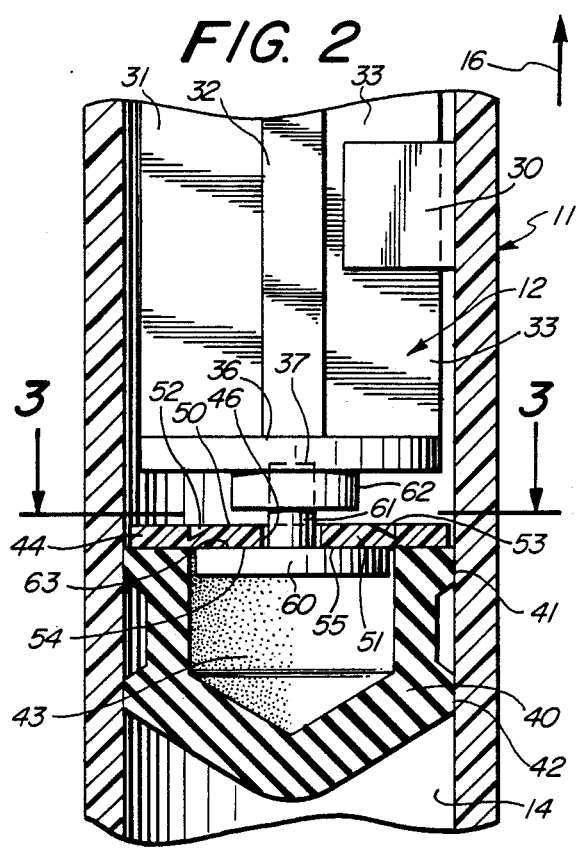
FIG. 2 sets forth a partial section view of a single use hypodermic syringe constructed in accordance with the present invention during the outward drawing stroke of the piston.

FIG. 2 sets forth a section view of a portion of hypodermic syringe 10 during the above-described drawing motion of piston 40. Accordingly, syringe 10 defines a cylindrical body 11 having a cylindrical bore 14 therein and supporting an inwardly extending lock member 30. Piston 40 is sealingly supported within bore 14 by a pair of outwardly extending seal members 41 and 42. Piston 40 defines a generally cylindrical interior cavity 43 and is preferably formed of a resilient rubber material or the like. A generally planar annular beam plate 44 is preferably formed of a brittle material such as acrylic and is configured to easily fit within bore 14. Beam plate 44 further defines a pair of inwardly extending beam members 50 and 51 defining an aperture 46 therebetween and joined to beam plate 44 at a pair of fulcrum points 52 and 53 respectively. Beam plate 44 further defines an aperture 47 (better seen in FIG. 3). In accordance with an important aspect of the present invention, aperture 47 is slightly larger than the diameter of cavity 43.

Driver 12 comprises a quartet of elongated generally rectangular ribs 31, 32, 33 and 34 (the latter not shown) arranged in a mutually perpendicular relationship. Driver 12 further defines a generally cylindrical end flange 36 joined to ribs 31 through 34 and a generally cylindrical breaker ring 62. In accordance with an important aspect of the present invention, breaker ring 62 defines a cross section substantially smaller than cavity 43 but larger than aperture 46 between beams 50 and 51. A retractor head 60 defines a generally planar cylindrical member having a cross section slightly smaller than cavity 43 together with a generally cylindrical retractor shaft 61 extending upwardly from retractor head 60 through aperture 46. Retractor shaft 61 is received and secured within recess 37 of drive 12 to provide a secure attachment between retractor head 60 and driver 12.

In the position shown in FIG. 2, driver 12 is being drawn upwardly in the direction indicated by arrow 16 at the initiation of the above-described filling operation of bore 14. As mentioned above, the drawing motion of driver 12 causes surface 63 of retractor head 60 to be pulled against surfaces 54 and 55 of beam members 50 and 51 respectively. In accordance with an important aspect of the present invention, the application of force between retractor head 60 and beams 50 and 51 close to fulcrum 52 and 53 respectively applies a bending moment to beams 50 and 51 through short lever arms which beams 50 and 51 can sustain. Accordingly, drawing motion of driver 12 causes beam plate 44 to withstand the force coupled by retractor head 60 and permits beam plate 44 and piston 40 to be drawn upwardly in the direction of arrow 16 within bore 14 of syringe body 11.

Figure 3:
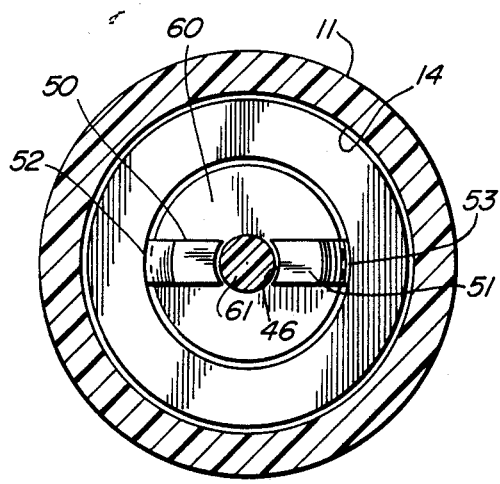
FIG. 3 sets forth a cross section view of the present invention single use hypodermic syringe taken along section lines 3—3 in FIG. 2.

FIG. 3 sets forth a cross section view of the embodiment of FIG. 2 taken along section lines 3—3. Cylindrical syringe body 11 defines an interior bore 14 within which an annular beam plate 44 is received. As described above, beam plate 44 defines a center aperture 47 and a pair of inwardly extending beam members 50 and 51. Beam members 50 and 51 define an aperture 46 therebetween. Beam members 50 and 51 are joined to beam plate 44 at a pair of fulcrum points 52 and 53 respectively. Retractor head 60, defining a generally cylindrical planar member, is captivated beneath beam members 50 and 51 and defines an upwardly extending cylindrical retractor shaft 61 which extends between beam members 50 and 51 through aperture 46.

Figure 4:
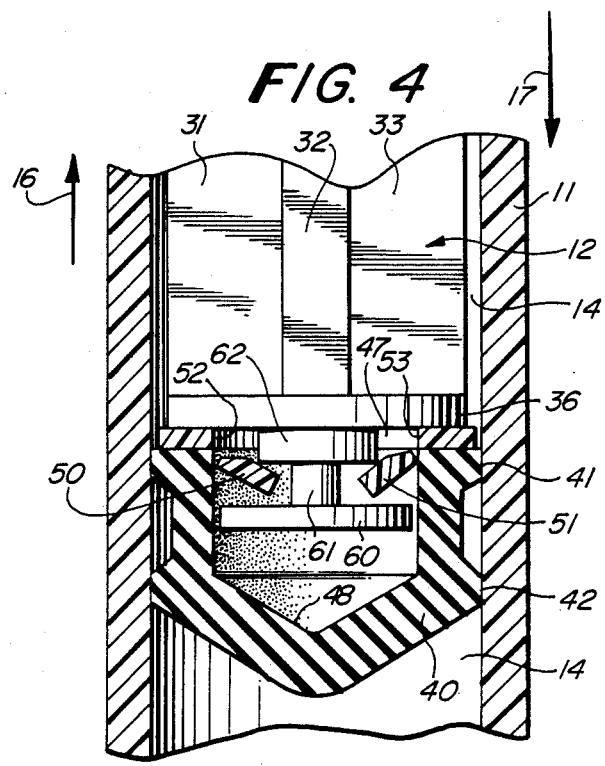
FIG. 4 sets forth a partial section view of the present invention single use hypodermic syringe at the initiation of a forward stroke of the piston.

FIG. 4 sets forth a partial section view of hypodermic syringe 10 showing the position of driver 12, retractor head 61, and piston 40 at the initiation of a downward stroke of driver 12 to cause the fluid within bore 14 to be expelled as described above. The downward motion of driver 12 in the direction indicated by arrow 17 forces breaker ring 62 against beam members 50 and 51. Because the diameter of breaker ring 62 is substantially less than that of retractor head 60, the forces in the direction of arrow 17 against beam members 50 and 51 are applied a substantial distance from fulcrums 52 and 53 respectively. As a result, the reduced diameter of breaker ring 62 causes the downward force to be applied to beam members 50 and 51 through longer lever arms which impose greater bending moments upon the beams. Accordingly, with the downward force applied to beam members 50 and 51 by breaker ring 62, the beam members are unable to support the greater bending moments of the applied forces and fracture at fulcrums 52 and 53 respectively causing beam members 50 and 51 to be broken from the remainder of beam plate 44. In the position shown in FIG. 4, this breakage of beam members 50 and 51 has just occurred and the continuing downward motion of driver 12 in the direction indicated by arrow 17 will bring retractor head 60 into contact with tapered surface 48 of cavity 43. Thereafter, the force applied by driver 12 to retractor head 60 is directly applied to piston 40 causing a corresponding downward motion of piston 40 which in turn expels the captivated fluid within bore 14 in accordance with the above-described operation.

At the completion of the downward stroke, the fluid captivated within bore 14 has been expelled and beam members 50 and 51 are completely severed from beam plate 44. In accordance with an important aspect of the present invention, a subsequent drawing motion of driver 12 in the direction indicated by arrow 16, which would otherwise cause a corresponding drawing motion upwardly of piston 40, is no longer effective because of the absence of the beam members 50 and 51. As a result, any drawing motion of driver 12 in the direction indicated by arrow 16 subsequent to a downward motion in the direction indicated by arrow 17 simply withdraws retractor shaft 61 and retractor head 60 from the interior of cavity 43 through aperture 47 in beam plate 44. Thus, piston 40 remains fixed at the bottommost portion of bore 14 (better considered by examination of FIG. 1). As a result, the present invention syringe 10 is rendered completely inoperative once beam members 50 and 51 have been broken and syringe 10 is incapable of further use as piston 40 remains immovably lodged at the bottommost portion of bore 14.

FIG. 5 sets forth an alternate embodiment of the present invention single use syringe which is generally identical to the embodiment set forth in FIGS. 1 through 4 in that a generally cylindrical syringe body 11 defines a cylindrical bore 14 and a driver 12 constructed in accordance with the above-described driver structure defines a flange 36 and a quartet of support ribs 31 through 34. Piston 40 is constructed in accordance with the above-described embodiment and defines a pair of seal members 41 and 42 and an interior cavity 43. In further accordance with the above-described embodiment, the embodiment of FIG. 5 includes a generally planar cylindrical retractor head 60 joined to breaker ring 62 by a retractor shaft 61. Retractor head 60, retractor shaft 61, and breaker ring 62 are substantially identical in the embodiment of FIG. 5 to that set forth in the embodiment of FIGS. 1 through 4 with the exception that retractor shaft 61 is somewhat shorter in the embodiment of FIG. 5. A beam plate 74, formed of a brittle material such as acrylic, defines a generally planar annular member having a pair of inwardly extending beam members 70 and 71. Beam members 70 and 71 are joined to beam plate 74 at a pair of fulcrums 72 and 73. Beam members 70 and 71 further define a pair of angled surfaces 75 and 76 respectively. As can be seen by comparison of FIG. 5 and FIG. 2, the structure of beam plate 74 is substantially the same as that of beam plate 44 with the exception of angled surfaces 75 and 76.

The operation of the alternate embodiment of FIG. 5 is substantially the same as that described above for the embodiment shown in FIGS. 1 through 4 with the exception that beams 70 and 71 are captivated between breaker ring 62 and retractor head 60. On the drawing stroke, no bending moments are applied to beams 70 and 71 due to this captivation. Thus, the beams are able to sustain the drawing force. On the downward stroke, however, angled surfaces 75 and 76 of beam members 70 and 71 respectively permit beams 70 and 71 to bend between retractor head 60 and breaker ring 62. In essence, the presence of angled surfaces 75 and 76 provides a clearance for the pivotal motion of beam members 70 and 71 during the downward stroke which results in a force application through longer level arms breaking beams 70 and 71 in the manner shown in FIG. 4. In all other respects, the operation of the alternate embodiment shown in FIG. 5 is identical to that described above for the embodiment shown in FIGS. 1 through 4.

FIG. 6 sets forth an alternate embodiment of the present invention single use syringe which makes use of a different coupling mechanism between the driver and piston assembly. Accordingly, cylindrical body 11 defines an interior cylindrical bore 14 which supports a piston 40 preferably fabricated of a resilient rubber or plastic material. Piston 40 further defines a pair of outwardly extending seals 41 and 42 as well as a cone-shaped surface 45. An internal cavity 43 is formed within piston 40 and terminates in a generally tapered surface 90. An elastic disk 85 preferably formed of a resilient rubber or plastic material and having a generally planar construction is secured to the upper portion of piston 40 by an adhesive bonding or the like. Elastic disk 85 further defines a center aperture 86. A driver 12, generally constructed in accordance with the foregoing described embodiments of driver 12, defines a quartet of generally rectangular ribs 31, 32 and 33 (the latter not shown) arranged in a mutually joined perpendicular arrangement. A generally cylindrical end flange 36 is joined to the lower end portions of ribs 31 through 34. End flange 36 and driver 12 further define an inwardly extending recess 37. A cylindrical blade disk 80 is secured to the lower surface of end flange 36 and defines a quartet of radially extending slots 101, 102, 103 and 104 (the latter seen in FIG. 7). Blade disk 80 further defines a center aperture 87. A quartet of cutting blades 81, 82, 83 and 84 (the latter seen in FIG. 7) are supported within slots 101 through 104 respectively and extend downwardly from end flange 36 toward piston 40. In accordance with an important aspect of the present invention, blades 81 through 84 define angled cutting edges 91 through 94 respectively which taper generally upward and inwardly. A cylindrical retractor head 95 sized to fit within cavity 43 is supported within cavity 43 beneath elastic disk 85 and includes an upwardly extending generally cylindrical retractor shaft 96. Retractor shaft 96 passes through aperture 86 in elastic disk 85 and aperture 87 in blade disk 80 to be received within recess 37 of driver 12. Retractor shaft 96 is bonded within recess 37 by a force-fit, or adhesive binding, or the like.

In operation, the alternate embodiment shown in FIGS. 6 through 9 is operative in much the same manner described above for the embodiments shown in FIGS. 1 through 5 in that the syringe is initially received by the medical practitioner with piston 40 at the bottommost portion of cylindrical bore 14. In use as described above and with reference to FIG. 1 together with FIG. 6, driver 12 is drawn outwardly from syringe body 11 in the direction indicated by arrow 16 to draw a predetermined quantity of to-be-injected fluid into bore 14.

Returning to FIG. 6, the relative positions of components shown correspond to those assumed by the present invention structure as driver 12 is drawn outwardly with respect to syringe body 11 pulling piston 40 in the upward direction indicated by arrow 16. As can be seen, elastic disk 85 captivates retractor head 95 within cavity 43 of piston 40. Thus, the drawing force applied to driver 12 is coupled by retractor shaft 96 and retractor head 95 to elastic disk 85 and in turn to piston 40. It should be noted that during the above-described drawing motion blades 81 through 84 are not in contact with disk 85. Thus, above-described drawing operation may be completed without any effect upon elastic disk 85.

Once the desired quantity of to-be-injected fluid is drawn into bore 14 driver 12 is forced downwardly within syringe body 11 in the direction indicated by arrow 97 which causes retractor head 95 to move downwardly to the dashed line position shown in FIG. 6. Correspondingly, the downward motion of driver 12 and retractor head 95 forces blades 81 through 84 downwardly against elastic disk 85. The presence of cutting edges 91 through 94 respectively of blades 81 through 84 causes elastic disk 85 to be slit beneath each of cutting blades 81 through 84 as the cutting blades move downwardly to the dashed line positions shown in FIG. 6.

FIG. 7 sets forth a section view of the embodiment of FIG. 6 taken along section lines 7—7 in FIG. 6. Cylindrical body 11 supports blade disk 80 which in turn defines a quartet of orthogonally oriented radially extending slots 101 through 104. Slots 101 through 104 support cutting blades 81 through 84 respectively which in turn define respective cutting edges 91 through 94. Blade disk 80 defines a center aperture 87 through which retractor shaft 96 extends.

FIGS. 7 and 8 show partial respective views of the operation of the embodiment shown in FIGS. 6 and 7 of the present invention single use syringe. It should be understood that, in FIGS. 8 and 9, cylindrical body 11 is not shown to permit examination and discussion of the coupling between driver 12 and piston 40. Accordingly and with reference to FIG. 8, piston 40 defines annular seals 41 and 42 and cone surface 45. Elastic disk 85 defines a center aperture 86 and is bonded to seal 41 of piston 40. Retractor shaft 96 extends upwardly through aperture 86 in elastic disk 85 and is received within and secured to flange 36 and the remainder of driver 12 as described above. Driver 12 defines a quartet of outwardly extending ribs 31 through 34 and end flange 36. A blade disk 80 defines a quartet of radially extending slots 101 through 104 (better seen in FIG. 7). A quartet of cutting blades 81 through 84 (better seen in FIG. 7) are secured within slots 101 through 104 respectively.

In the position shown in FIG. 8, the above-described drawing operation is complete and bore 14 (see FIG. 6) is filled with to-be-injected fluid. FIG. 8 sets forth the initiation of the downward stroke of driver 12 in the direction indicated by arrow 25. As mentioned above, the downward motion of driver 12 forces cutting blades 81 through 84 against elastic disk 85 creating a corresponding plurality of slits 111 through 114 within elastic disk 85.

As the downward motion in the direction 25 continues, blades 81 through 84 are passed completely through elastic disk 85 forming a plurality of slits 111 through 114 respectively. The downward motion of driver 12 continues forcing piston 40 downwardly within the interior bore of the hypodermic syringe and expelling the to-be-injected fluid from the bore interior.

FIG. 9 sets forth the operation of the embodiment shown in FIG. 7 which results once piston 40 has been driven to the bottom of the interior bore of the hypodermic syringe and the user attempts to reuse the present invention syringe by drawing driver 12 upwardly within the syringe body in the direction shown by arrow 26. As driver 12 is pulled upwardly, the drawing force is, as mentioned above, coupled by retractor shaft 96 to retractor head 95. Prior to the formation of slits 111 through 114 by blades 81 through 84 during the downward stroke described above, elastic disk 85 serve to couple the drawing force from retractor head 95 to piston 40. In the situation shown in FIG. 9, however, slits 111 and 112 as well as identical slits 113 and 114 (not shown) simply expand in the manner indicated due to the elasticity of elastic disk 85 and the drawing force imparted to driver 12 simply pulls retractor head 85 free of piston 40 and elastic disk 85. As a result, piston 40 cannot be withdrawn within bore 14 as is necessary to draw fluid into the present invention hypodermic syringe. As a result, the first use of the present invention hypodermic syringe renders the syringe unusable and precludes unauthorized use of the syringe.

In each of the embodiments shown, the frictional characteristics of the piston against the inside of the syringe body bore and the strengths of the coupling mechanism between the piston and the driver to drawing and injecting forces are matched to provide breakage only in response to injecting forces.

What has been shown is a convenient inexpensive and easy to use hypodermic syringe which is constructed to preclude use after its initial operation. Several embodiments have been shown which are operative to sever the coupling between the driver member and the piston to leave the piston fixed at the bottom of the syringe bore and preclude any subsequent use.

While particular embodiments of the invention have been shown and described, it will be obvious to those skilled in the art that changes and modifications may be made without departing from the invention in its broader aspects. Therefore the aim in the appended claims is to cover all such changes and modifications as fall within the true spirit and scope of the invention.

What is claimed is:

1. A single use hypodermic syringe comprising:
    an elongated syringe body defining an interior syringe bore;
    a hollow needle supported by said syringe body in communication with said syringe bore;
    a piston defining an internal cavity having an open end facing said piston driver sealingly fitted within said syringe bore and movable therein in a first direction away from said needle and a second direction toward said needle;
    a piston driver having a first end extending into said syringe bore; and
    single use coupling means for coupling said piston driver to said piston during initial movement of said piston driver in said first direction followed by movement in said second direction and fracturably releasing said piston during movement of said driver in said first direction thereafter, said single use coupling means including a plurality of inwardly extending fracturable members supported upon said piston driver and interlocking said piston and said first end of said piston driver.

2. A single use hypodermic syringe as set forth in claim 1 wherein said piston defines an internal cavity having an open end facing said piston driver and wherein said single use coupling means includes:
- a retractor head formed on said first end of said piston driver received within said cavity;
- a retractor shaft connecting said retractor head to said first end of said piston driver;
- captivation means coupled to said piston and extending between said retractor head and said first end of said piston driver to captivate said retractor head within said cavity; and
- severing means operative during motion of said piston driver in said second direction to sever said captivation means and release said captivation.

3. A single use syringe as set forth in claim 2 wherein said captivation means includes a beam plate formed of a brittle material and defining an aperture larger than said retractor head and supporting said plurality of inwardly extending fracturable members each having end portions spaced from said retractor shaft and wherein said severing means include a breaker ring extending from said first end of said piston driver having a cross section substantially less than said opening in said piston but sufficient to contact said ends of said fracturable members when said piston driver is moved in said second direction.

4. A single use hypodermic syringe as set forth in claim 3 wherein said fracturable members are beam members of said captivation means define reduced thickness fulcrum portions joining said beam members to the remainder of said beam plate of said opening.

5. A single use hypodermic syringe as set forth in claim 4 wherein said plurality of beam members includes a pair of oppositely positioned beam members.

6. A single use hypodermic syringe as set forth in claim 5 wherein said beam members each define generally rectangular cross sections and wherein said ends of said beam members each define angled surfaces angled away from said retractor head.

7. A single use hypodermic syringe as set forth in claim 2 wherein said captivation means include an elastic disk joined to said piston and extending over said opening in said piston and defining an aperture through which said retractor shaft extends and wherein said severing means include a plurality of cutting blades extending from said first end of said piston driver operative to cut a corresponding plurality of slits in said elastic disk when said piston driver is moved in said second direction.

8. A single use hypodermic syringe as set forth in claim 7 wherein said plurality of blades are radially disposed with respect to said retractor shaft.

9. A single use hypodermic syringe as set forth in claim 8 wherein said plurality of blades each define angled cutting edges.

10. A single use hypodermic syringe as set forth in claim 9 wherein said plurality of blades include four mutually perpendicular blades.

* * * * *